United States Patent [19]
Pagels et al.

[11] Patent Number: 5,641,682
[45] Date of Patent: Jun. 24, 1997

[54] APPARATUS AND METHOD FOR AUTOMATICALLY PROCESSING DRIED BLOOD SPOTS IN HIV-1 TESTING

[75] Inventors: William Pagels, Oceanport; Noel Rolon, Belle Mead, both of N.J.

[73] Assignee: Ortho Pharmaceutical Corporation, Bridgewater, N.J.

[21] Appl. No.: 514,647

[22] Filed: Aug. 14, 1995

[51] Int. Cl.$^6$ .................................................. G01N 35/02
[52] U.S. Cl. .......................... 436/43; 436/46; 436/48; 436/50; 436/55; 436/63; 422/63; 422/64; 422/65; 422/66; 422/67
[58] Field of Search .................. 436/43, 46, 48, 436/50, 55, 63; 422/63, 64, 65, 66, 67

[56] References Cited

U.S. PATENT DOCUMENTS

| 4,341,735 | 7/1982 | Seifried ........................... 422/66 |
| 4,568,519 | 2/1986 | Hamilton et al. .................. 422/63 |
| 4,584,275 | 4/1986 | Okano et al. ..................... 436/46 |
| 4,820,491 | 4/1989 | Khoje et al. ...................... 422/63 |
| 4,855,109 | 8/1989 | Muraishi et al. ................... 436/45 |
| 5,122,343 | 6/1992 | Ishizaka et al. .................... 422/63 |
| 5,196,168 | 3/1993 | Muszak et al. .................... 422/63 |

FOREIGN PATENT DOCUMENTS

0717283  6/1996  European Pat. Off. .

Primary Examiner—Jill Warden
Assistant Examiner—Sharidan Carrillo
Attorney, Agent, or Firm—Paul A. Coletti

[57] ABSTRACT

An apparatus and method for automatically identifying, handling, tracking, and processing dried blood samples in HIV-1 testing are disclosed. Dried blood samples are punched from test cards into incubation receptacles for incubation and further testing. Optionally, the location on the test card to be punched may be manually, semi-automatically or automatically selected, ranked, and punched in order of preference. Test results corresponding to a particular test subject are automatically tracked and reported while maintaining the anonymity of the subject.

24 Claims, 3 Drawing Sheets

APPARATUS AND METHOD FOR AUTOMATICALLY PROCESSING DRIED BLOOD SPOTS IN HIV-1 TESTING

FIELD OF THE INVENTION

This invention generally relates to the testing of blood samples for the detection of particular characteristics of the blood. More particularly, this invention relates to the handling, tracking and processing of blood samples during such testing. Even more particularly, this invention relates to the automated handling, identification, tracking and processing of blood samples collected on filter paper for the detection of the HIV-1 virus.

BACKGROUND OF THE INVENTION

AIDS (Acquired Immune Deficiency Syndrome) is viewed as one of the most serious modern-day health issue affecting society. Since there is presently no known cure for the disease, early detection and treatment of the HIV virus provides the best chance of helping a patient to prolong his or her life by delaying onset of the disease. In addition, early detection is crucial to preventing the spread of the virus itself.

Although early detection of the virus is vitally important, only about 8% of adult Americans are tested annually. Individuals have been reluctant to submit to testing because, among other things, they fear that a positive test result will not be kept confidential. It is currently estimated that if a diagnostic procedure which could assure an individual's confidentiality was available, the number of at-risk individuals being tested for the HIV virus would increase to approximately 29%.

The present invention relates to a confidential at-home testing system for determining whether an individual may be carrying the HIV virus. An individual uses the at-home system by purchasing a test kit at a pharmacy or other retail outlet. The test kit contains, among other items, a test card for carrying a sample of the individual's blood to a testing lab. The individual places several drops of blood on a designated area on the test card comprising filter paper, or other suitable material, while at home. The individual then mails or otherwise delivers or transmits the test card to a central laboratory for testing. Several days later, the individual calls a central phone number or otherwise contacts the central laboratory to get test results and to receive counseling on the HIV virus and AIDS.

In the case of individuals testing positive for the HIV virus, incoming calls placed to the central phone number are routed to telesets staffed by live counselors for handling. Since numerous telephone calls must be handled simultaneously by the system, each caller that has tested positive for the HIV virus will be routed to a teleset associated with one of a plurality of live counselors.

In order to maintain the effectiveness and integrity of a testing system such as the one described above, the system should have mechanisms for monitoring: (i) whether the individual's test specimen (typically in the form of a test card or dried blood spot (DBS) punched from the test card) has been received by the central laboratory for testing; (ii) whether testing has commenced or has been completed on the specimens received; (iii) the location of the specimen at any given time; (iv) whether an individual's test results have been reported to the individual and, if so, how many times; (v) whether an individual has been counselled by the testing system and, if so, concerning which topics, and how many times; and (vi) the length of time since the individual's test results were analyzed by the testing lab. In addition to monitoring these parameters, the testing system must also be able to deliver confidential test results and counselling to numerous individuals over the telephone in an efficient and cost-effective manner.

In the case where a client has tested HIV positive, a live counselor will not only inform the client-caller of the test results, but may also counsel the client on various aspects of HIV and AIDS. In order for the live counselor to handle the call properly, the counselor must be apprised of all available laboratory information about the client-caller (e.g., the date the testing laboratory received the client's specimen, the date the testing laboratory completed its testing of the client's specimen, whether the client has called the counseling center previously and, if so, the date and time of such calls and a list of the topics discussed during such calls, etc.) simultaneous to call. A workstation positioned in front of each live counselor is provided for displaying such information about the client-caller.

In view of the foregoing, it is apparent that the need exists for a system which automatically identifies, handles, tracks and processes blood samples in HIV-1 testing as quickly and as accurately as existing HIV testing techniques will permit. Moreover, because the blood samples provided by a non-professional user will vary greatly in size, shape and blood concentration, the need exists for a system which has the capability of automatically selecting the portion of the blood sample which will return the most accurate result as well as yield the greatest number of dried blood spots from the blood provided.

To date, certain process steps in the testing of blood samples, particularly blood samples which are in the form of dried blood spots (DBS) on filter paper, have been entirely manual or semi-automated process steps. One such step comprises punching a substantially circular DBS of a predetermined diameter from filter paper typically found on a test card. Although certain manual and semi-automatic devices exist to carry out this process, such devices generally require an operator to physically position the test card in a standard male die-type punch. These devices comprise dies which are dedicated to punching DBSs of a single size. Typically, these devices punch a ¼" diameter DBS from a blood sample spot which may range from ½" to ⅝" diameter. Two such devices are produced by I.E.M. of North Hollywood, Calif. and BSD Technologies International of Austria. These punches are typically tooled such that a DBS is punched from a preset location on the test card. The punched DBS is also generally smaller in size than that of the DBS itself.

Because individual users will deposit blood samples of varying amounts and shapes on different areas of the card, there will exist areas on the card which contain higher blood concentrations more desirable for testing purposes. Because current semiautomatic punching devices do not allow for the selection of the most desirable DBS location within the blood sample there becomes a need for an apparatus and method for automatically punching DBSs from that area.

In addition, because the amount of blood sample available to the testing facility is limited, it is desirable to obtain as many DBSs from each blood sample as possible. Accordingly, there exists a need for a device that may punch DBSs which have a smaller surface area than a ¼" diameter DBS.

Furthermore, in order to speed the overall testing process while achieving maximum accuracy of testing, there exists the need for a device which automatically (1) transports a test card to a punching station; (2) selects the most desirable area of a blood spot to be punched; (3) punches a DBS directly into a test receptacle (such as an elution plate or Western Blot tray); (4) transports the test receptacle for further processing; and (5) tracks the identity and location of the particular DBS throughout the process and makes available the test results, all while maintaining the anonymity of the test subject.

Accordingly, it is an object of the present invention to provide a system which automatically identifies, handles, tracks and processes blood samples in the form of dried blood spots.

It is a further object of this invention to provide a system which compiles and reports test result data related to particular blood samples.

It is yet a further object of this invention to provide an automatic system which automatically handles test cards containing blood samples and incubation receptacles, punches DBSs of a desirable or optimum size and location on the test card into individual incubation receptacles, tracks the identity and location of an individual DBS at any time and reports such information to a central monitoring site for delivery of test results.

It is still a further object of this invention to provide an automatic system which, prior to punching, analyzes a blood sample contained on a test card and detects a preferred area to be punched and utilized for testing purposes.

It is yet a further object of this invention to provide an automatic system for punching optimum or desired DBSs from test cards directly into individual incubation receptacles at a rapid rate while maximizing the speed and reliability of such a process.

These and other objects of the present invention will become apparent upon study of the accompanying drawings and description of the invention.

SUMMARY OF THE INVENTION

The present invention provides an apparatus and method which automatically identifies, handles, tracks and processes blood samples in testing for the HIV-1 virus. More specifically, this invention automatically identifies a test card containing a blood sample or samples and transports the test card to a punching station. Contemporaneously, an incubation tray comprising one or more incubation receptacles is identified and transported to the punching station. Once the test card reaches the punching station, the blood samples are analyzed to determine a preferred optimal area to punch a dried blood spot (DBS) to be used for testing. Contemporaneously with the identification of the area to be punched, the incubation tray is positioned such that a single incubation receptacle is positioned to receive the DBS being punched. The DBS is then punched directly into the incubation receptacle. The location of the incubation receptacle and identity of the DBS in that receptacle is then identified and stored for future reference. It is also possible to punch multiple DBSs of various sizes and shapes from one or more of the blood samples present on the same test card. Additional DBSs may be analyzed and punched from the same test card into additional individual incubation receptacles as is desired. Each DBS is selected and its identity and location is tracked as with the original DBS.

Once the desired number of DBSs have been punched from the test card, the test card may be retained for further analysis or discarded. A new test card is then transported to the punching station and the process of identification, analysis of blood sample and punching are continued. Once all of the receptacles in the incubation tray are filled with DBSs, the tray is automatically transported to an incubation chamber. After incubation, the tray may be transported to other stations for further testing and evaluation. Test results of each DBS are then compiled, together with the identity of each DBS. The test results and identifying information may then be sent to a central monitoring site for reporting to the test subject, who thought this test period is anonymous to personnel at the test laboratory, and is only identified by a serial number of the test card.

BRIEF DESCRIPTION OF THE DRAWINGS

There are shown in the drawings aspects of certain preferred embodiments, it being understood that the invention is not limited to the precise embodiments and instrumentalities shown.

DETAILED DESCRIPTION

Figure 1:
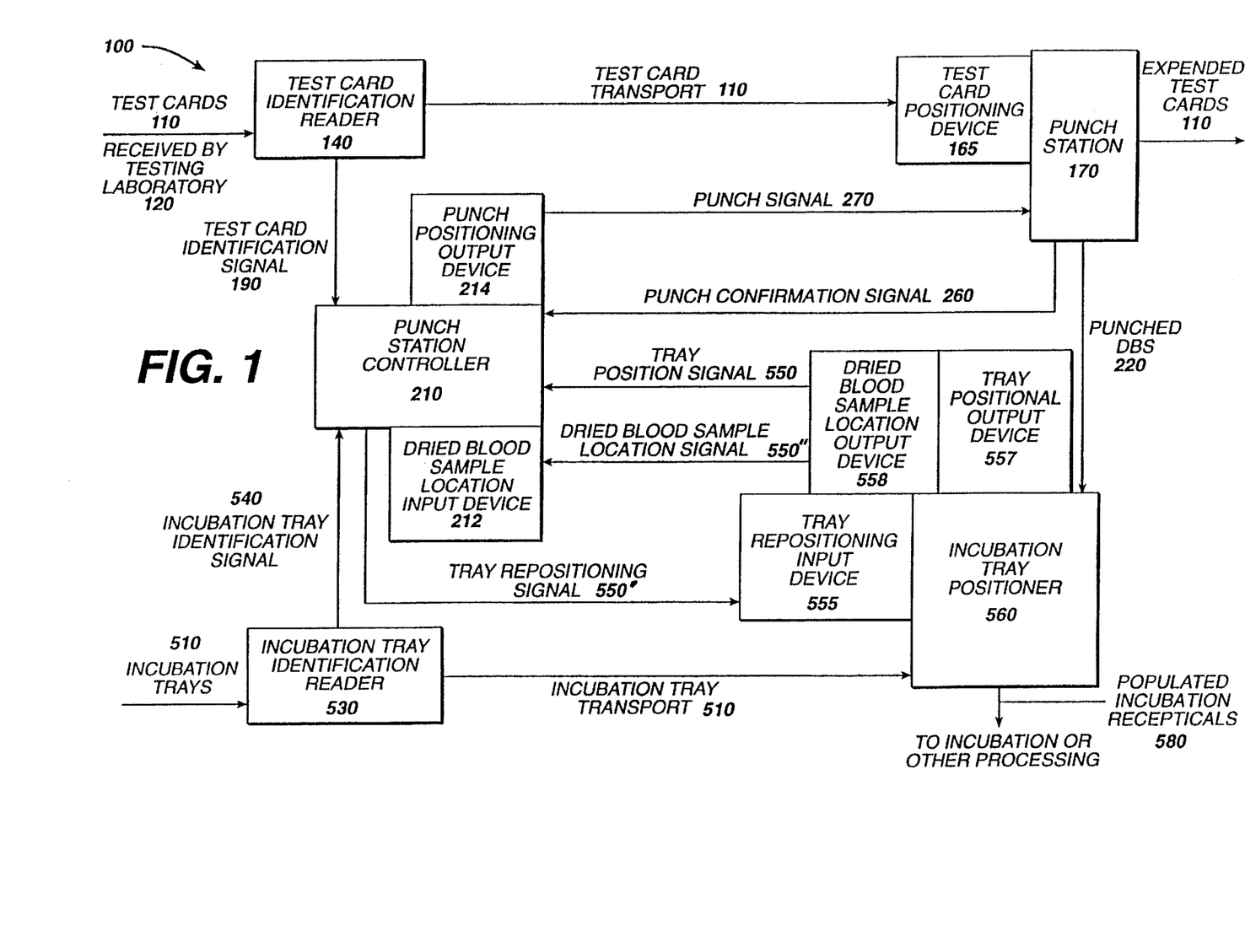
FIG. 1 is a schematic of one embodiment of an automated system for identifying, handling, tracking and processing blood samples in accordance with the present invention.

It is noted that what follows illustrates the use of the automated system 100 for HIV testing. However, this automated system could be applied for use with other analytes contained on a test card. Additionally, the analyte may not be blood in origin. Referring now to the drawings in detail, wherein like reference numerals indicate like elements, there is seen in FIG. 1 an automated system 100 for identifying, handling, tracking and processing blood samples deposited by individuals on designated areas of a test card 110. Test cards 110 may be any device suitable for collecting and retaining blood or uriological fluid samples such as the test cards described in European Patent Application EP 0717283A2, published Jun. 19, 1996, which is incorporated herein by reference. The area of test card 110 which contains the blood sample may be made of filter paper or any other material suitable for retaining the blood sample and for testing purposes. Each test card 110 also bears an identification device, such as a personal identification number (PIN), generally stored in the form of a bar code magnetic strip ratio frequency system or other identification device. Exemplary of a suitable identification means and systems are also described in copending U.S. patent application Ser. No. 08/366,785 "SYSTEM FOR TRACKING SECURE MEDICAL TEST CARD, which applications are incorporated herein by reference.

Test cards 110 contain blood samples which have been prepared by test subjects with the aid of an at-home HIV test kit. Test cards 110 are received by a testing laboratory 120 and loaded into a test card identification reader 140 for processing. Each test card 110 may contain one or more blood samples from the same individual. Each sample is deposited by the individual onto a designated sample area on the filter paper portion of the test card. In the embodiment described herein, test card 110 will contain three designated sample areas (a right hand, left hand and center designated sample areas) each containing a separate blood sample. Each blood sample may be almost any size but typically are between approximately ½" and ⅝" in diameter.

Each test card 110 is analyzed by test card identification reader 140 in order to detect the identification number of test card 110 and, accordingly, the dried blood samples thereon. Test card reader 140 also may comprise test card identification input and output devices. The input and output devices read the test card identification device and produce test card identification signal 190, respectively. Test card reader 140 processes the detected test card identification and converts the identification into test card identification signal 190.

Incubation trays 510, which comprise one or more incubation receptacles into which the DBSs are punched, also comprise an identification device, such as a bar code. Trays 510 are introduced to incubation tray identification reader 530 in order to detect the identification of incubation tray 510. Tray identification reader 530 also may comprise tray identification input and output devices. These input and output devices read the incubation tray identification device and produce an incubation tray identification signal 540, respectively. Incubation tray reader 530 processes the detected incubation tray identification and converts the identification into incubation tray signal 540. Both test card identification signal 190 and tray identification signal 540 are transmitted to and received by punch station controller 210.

Test card 110 is then transported from test card identification reader 140 to punch station 170. Punch station 170 comprises a punch and a test card positioning device which positions test card 110 in punch station 170 so as to allow for the desired portion of the dried blood sample to be punched. Punch station 170 further comprises a punch input device and a punch signal confirmation output device. The input device receives a punch signal 270 from punch station controller 210 to punch a dried blood sample from test card 110 into an incubation receptacle at the appropriate time. The confirmation output device produces punch confirmation signal 260 once it is detected that test card 110 is properly positioned in punch station 170.

Prior to punching, incubation tray 530 is preferably transported to incubation tray positioner 560. Incubation tray positioner 560 comprises a tray repositioning input device, a tray position output device and a dried blood sample location output device. The repositioning input device receives a tray repositioning signal 550 from controller 210. Tray repositioning signal 550 comprises the location of the next available incubation tray receptacle into which dried blood sample 220 is to be punched. Upon receipt of repositioning signal 550, incubation tray 510 is repositioned so as to allow sample 220 to be deposited in the appropriate receptacle. The tray position output device produces tray position signal 550 indicating the location of incubation tray 510. Tray position signal 550 is transmitted to the controller. The dried blood sample location output device produces a dried blood sample location signal 550 which signal corresponds to the incubation tray receptacle or location into which dried blood sample 220 is punched.

Incubation tray positioner 560 transmits tray positioning signal 550 to controller 210. Controller 210, in turn, transmits tray repositioning signal 550 to incubation tray positioner 560 with the location of the next available incubation tray receptacle. Positioner 560 repositions tray 510 so that the appropriate receptacle is in position to receive dried blood sample 220. Once sample 220 has been punched, positioner 560 transmits dried blood sample location signal 550 to controller 210.

Punch station controller 210 essentially controls the punching operation of system 100. Controller 210 comprises a test card identification input device, a tray identification input device, a tray position input device, a tray repositioning output device, a dried blood sample location input device, a punch signal confirmation input device and a punch signal output device. Test card identification input device receives test card identification signal 190 from test card reader 140. Tray identification input device receives tray identification signal 540 from incubation reader 530. Tray position input device receives tray position signal 550 from incubation tray positioner 560. Tray repositioning output device produces tray repositioning signal 550 and transmits repositioning signal 550 to incubation tray positioner 560. Dried blood sample location input device receives said dried blood sample location signal 550 from incubation tray positioner 560. Punch signal confirmation input device receives punch confirmation signal 260 from punch station 170 once test card 110 and incubation tray 510 is properly positioned. Punch signal output device produces punch signal 270 once punch confirmation signal 260 is received by controller 210. Punch station 170 activates and punches test card 110 upon receipt of punch signal 270.

Once the supply of the dried blood sample available on a particular test card 110 is exhausted or otherwise not desired, test card 110 is transported from punch station 170 and a new test card is transported into punch station 170. Likewise, once all of the receptacles on a particular incubation tray 510 are utilized, fully populated or otherwise not desired, tray 510 is transported from incubation tray positioner 560 to incubation and/or other processing stations.

Figure 2:
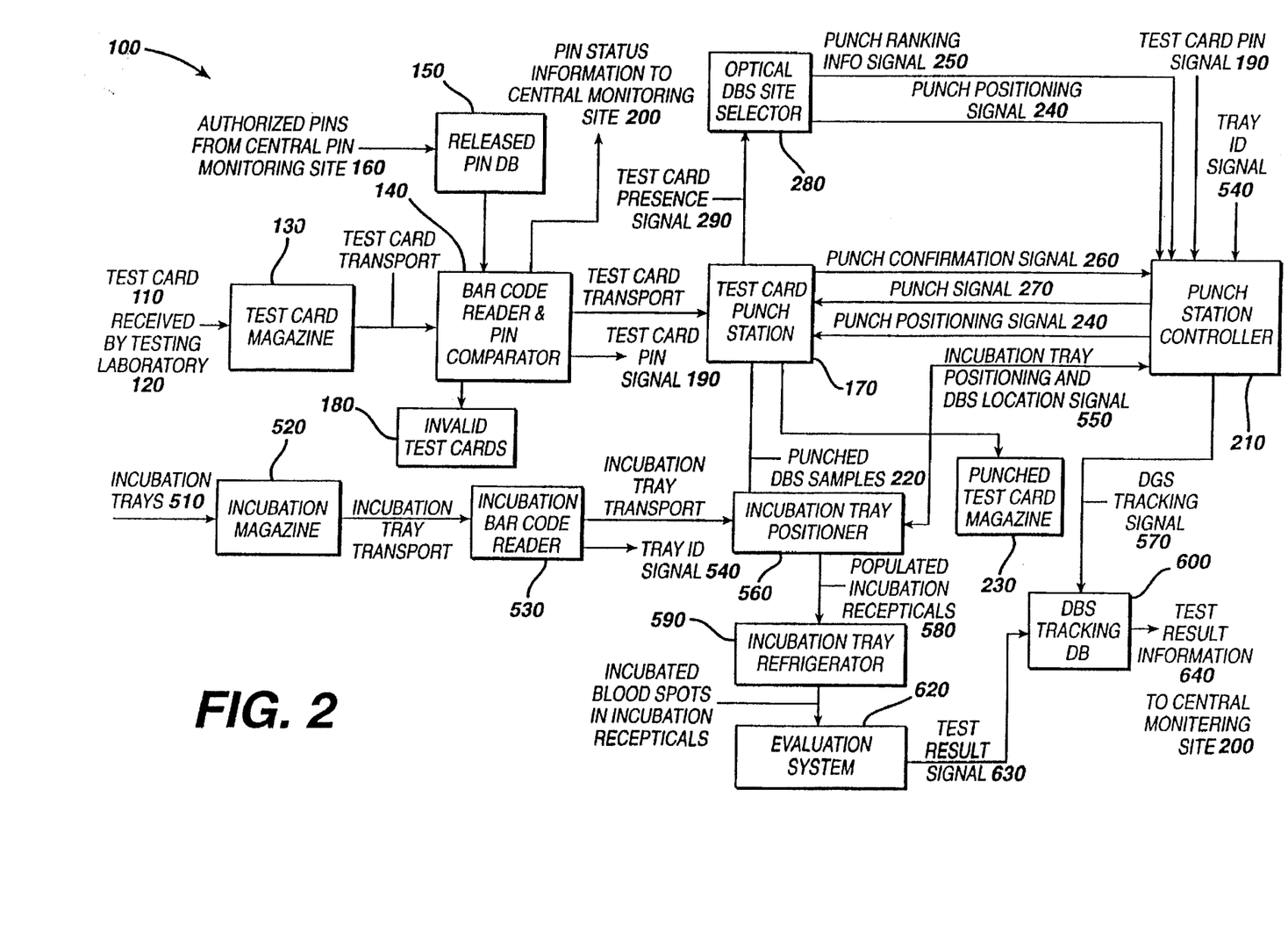
FIG. 2 is a schematic of an automated system for identifying, handling, tracking, processing and reporting test results associated with blood samples in accordance with the present invention.

Referring now to FIG. 2, there is shown another embodiment of this invention in the form of an automated system 100 for identifying, handling, tracking, processing and reporting test results related to blood samples.

In this embodiment, each test card 110 is transported from magazine 130 to an authorization and identification device such as bar code reader and PIN comparitor 140. The transport means described throughout this embodiment may comprise any suitable conveying means such as, for example, a continuous conveyor belt having adequately spaced flights affixed thereto in order to transport each test card 110 from a bottom fed magazine 130. Reader/comparitor 140 reads the PIN which identifies the individual test subject by scanning the bar code contained on test card 110. Reader/comparitor then compares the PIN to a list of authorized PINs in released PIN database 150. Released PIN database 150 is compiled from previously authorized PINs received from a central PIN monitoring site 160, described more fully in U.S. patent application Ser. No. 08/367,535 entitled "Automated System for Identifying Authorized System Users" which application is incorporated herein by reference. If the PIN read from test card 110 is recognized as a valid PIN from released PIN database 150, test card 110 is transported to dried blood spot (DBS) punch station 170. Additionally, a test card PIN signal 190 is transmitted to punch station controller 210, identifying the PIN corresponding to test card 110 next being transported to punch station 170. If the PIN is not recognized by released PIN database 150 as a valid PIN, test card 110 is passed to an invalid test card receptacle 180 and will not be processed further by system 100. In either instance, the validity or invalidity of each PIN and corresponding test card 110 is reported by signal 190 to central monitoring site 200.

Depending on the capacity of incubation trays 510 and cycle time of the overall system 100, incubation trays 510 are loaded into incubation tray magazine 520 by an operator of system 100. Incubation trays 510 may comprise from one to one hundred or more individual incubation receptacles.

Incubation trays 510 may comprise any suitable incubation device including an elution plate or a Western Blot tray depending upon the incubation testing that is to be carried out on each blood sample. The precise size, type or capacity of tray 510 employed is not critical as system 100 may be readily adapted by those skilled in the art to accommodate any of numerous configurations of incubation trays 510. Typically, each incubation receptacle contains a sufficient amount of buffer and one or more DBSs to create sufficient concentration ratios of blood sample to buffer.

Each tray 510 may bear an identification device such as a magnetic strip, radio frequency system or other identification device on which an identification code or number is stored which identifies the particular incubation tray 510 code, generally stored in the form of a bar code. Incubation trays 510 are transported from magazine 520 to incubation tray bar code reader 530. Reader 530 reads the identifying bar code on tray 510 and transmits a tray identification signal 540 to punch station controller 210. In addition to information identifying the particular tray 510, signal 540 may contain such information as the type of tray 510 being transported (e.g. elution plate, Western Blot tray, etc.) the number of receptacles in tray 510 and the physical layout of the receptacles (e.g. an 8×12 array in the case of an elution plate or a multiple well tray in the case of a Western Blot tray). Such information may then be used for automatically positioning tray 510 in incubation tray positioning means 560 for tracking individual blood samples.

Positioner 560 is oriented with respect to punch station 170 such that blood samples in the form of dried blood spots (DBSs) 220 may be punched directly into individual incubation receptacles contained on tray 510. Positioner 560 may comprise any suitable means for positioning each receptacle to capture a single DBS 220. For example, positioner 560 may comprise a standard X-Y positioning table located directly below punch station 170. Alternatively, positioner 560 may comprise a robotic handling device. In operation, positioner 560 would position a receptacle directly below punch station 170 such that DBS 220 is punched directly into the receptacle.

Incubation tray 510 transport means described throughout this embodiment may comprise any suitable conveying means such as, for example, a continuous conveyor belt having adequately spaced flights affixed thereto, in order to transport each tray 510 from incubation magazine 520.

In order to position and transport tray 510 during automatic operation, several incubation tray location signals 550 are exchanged between punch station controller 210 and incubation tray positioner 560.

For example, prior to a DBS 220 being punched from test card 110, an incubation tray positioning signal 550 is sent to punch station controller 210 to determine if another receptacle is available on tray 510 currently located at positioner 560. Controller 210 comprises signal 550 with tray 510 data received as tray identification signal 540 to determine the capacity and geometric configuration of tray 510. If another receptacle is available on tray 510, then a return tray positioning signal 550 is sent to positioners 560, which positions the next receptacle to receive the next DBS 220 from punch station 170. If another receptacle is not available on tray 510, the return signal 550 will indicate that tray 510 has reached capacity and positioner 560 will transport tray 510 to incubation chamber 590. Positioner 560 will then position an empty tray 510 into position to receive the next DBS 220.

Test card punch station 170 may comprise one or more high precision punches for punching DBS 220 from blood samples on test card 110. These punches may comprise any cutting device suitable for punching adequately sized DBSs 220 from filter papers as, for example, a male-female die. The punch may cut DBS 220 to any desired size or shape but preferably DBSs 220 are circles or discs which are between approximately ⅛" to ¼" in diameter.

New incubation techniques may require or allow for the utilization of numerous sizes, shapes and quantities of DBSs 220 as in U.S. application Ser. No. 08/367,046, entitled "Apparatus and Method for Testing Dried Blood Spots By the Western Blot Procedure", which application is incorporated herein by reference. Therefore, punch station 170 may also be adapted to produce such DBSs 220.

FIG. 3 depicts several configurations of DBS punch patterns in plan views. FIG. 3a depicts a typical circular DBS which diameter could range between approximately ⅛" to approximately ¼". FIG. 3b depicts two concentric DBSs 220 having an inner DBS 1010 punched from an outer DBS 1020. DBSs 1010 and 1020 may be punched simultaneously with a die having concentric male and female members alternatively, DBSs 1010 and 1020 can be produced in a two step process, first punching DBS 1010 from test card 110 and then punching DBS 1020 from test card 110. Yet another punching process would allow for the punching of DBS 1020 from test card 110 and repositioning DBS 1020 for punching in a second die to punch out DBS 1010.

Figure 3A:
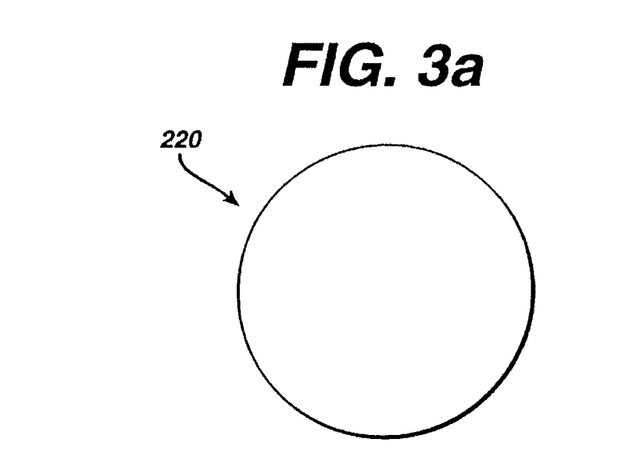
FIG. 3 is a plan view of the shapes of various dried blood spots produced by the present invention.
Figure 3B:
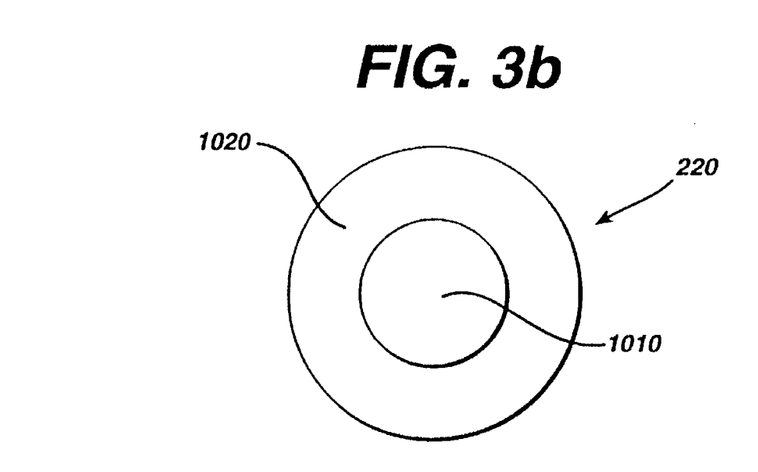
Figure 3C:
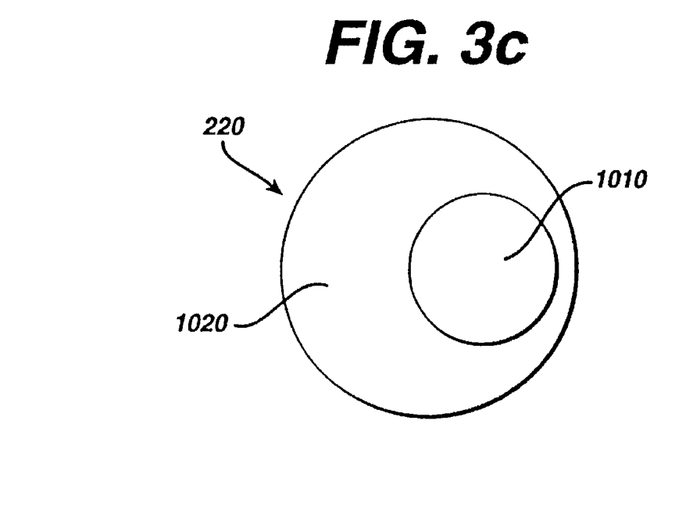
Figure 3D:
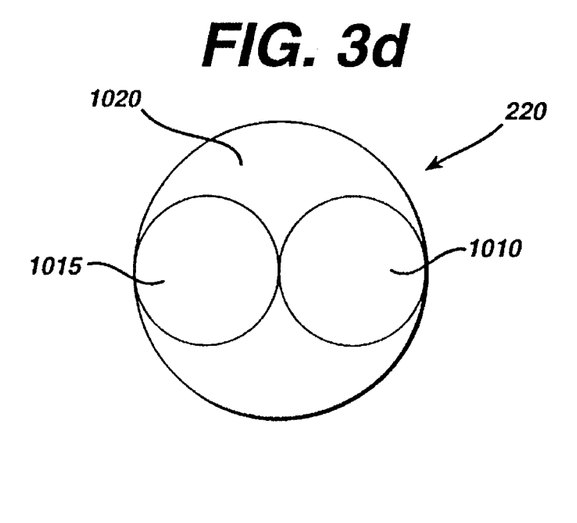

As is depicted in FIG. 3c, it is not necessary that inner and outer DBSs 1010 and 1020 be concentric. Similar processes used to punch the concentric DBSs 1010 and 1020 of FIG. 3b may also be used to punch non-concentric DBSs 1010 and 1020. Also, multiple non-concentric DBSs 1010 and 1015 may be punched from DBS 1020 in one, two or three step processes similar to those used to punch the DBSs of FIGS. 3b and 3c. However, it should be noted that any size, shape or number of DBSs may be punched from test card 110 provided that each DBS contains a sufficient amount of blood sample (which amount does correspond to DBS surface area) to assure accurate and reliable incubation processing.

For example, it is known that for the incubation processes employed with system 1010 generally DBSs of between approximately ⅛" and ¼" in diameter are suitable to produce accurate and reliable results. Since DBSs of ⅛" and ¼" diameter have an approximate surface area of 0.01227 in$^2$ and 0.04909 in$^2$ respectively, any shape of DBS having surface area approximately between 0.01227 in$^2$ and 0.04909 in$^2$ will be suitable for this invention. However, it should be noted that because the blood concentration per square area on each test card may vary, it is possible that other sizes, shapes and surface areas of DBSs are possible. Generally, as the blood concentration per square area increases the surface area of the DBS required to produce accurate and reliable results will decrease. Likewise, as the areas of blood concentration per square area decreases, the surface area of the DBS will increase.

Punch station 170 also comprises a test card positioner which is capable of aligning test card 110 to punch from test card 110 the desired or optimum filter paper location to form DBS 220. This positioner may comprise any suitable positioning device such as, for example, a standard computer controlled X-Y positioning table adapted for receiving, holding and discharging test card 110 to punched that card magazine 230. Alternatively, robotic systems may be utilized as devices for handling test cards 110, dried blood spots 220, incubation trays 510, or other materials required to be handled in automated system 100.

Punch station 170 operates as follows. Test card 110 is received from reader/comparitor 140 and positioned on a positioner such as an X-Y table. The location on the test card to be punched is identified by any manual, semi- automatic or fully automatic means described in further detail below. Preferably, this location corresponds to the optimal or "best" spot Of the blood samples deposited on test card 110. Once the best spot is identified, a punch positioning signal 240 is either manually or automatically transmitted to punch station controller 210. Punch positioning signal 240 comprises the location or coordinates of the blood sample to be punched, Optionally, a punch ranking information signal 250 is also transmitted from selector 280 to punch station controller 210. Signal 250 comprises the ranking of the location to be punched. The ranking relates to the level of desirability of a particular blood sample location. For example, the "best" spot may be punched first and assigned a ranking of one (1) which would correspond to the best sample taken from a particular test card 110. The next test spot may be assigned a ranking of two (2) corresponding to the second best sample taken from test card 110 and so on.

Accordingly, ranking signal 250 and test card PIN signal 190 are compiled in punch station controller 210 together with incubation tray identification signal 540. Based on the coordinates received from controller 210 in positioning signal 240, the test card positioner of punch station 170 aligns the test card with the die or punch head for punching of the location of the blood sample previously identified. Alternatively, the test card positioner may be replaced with a movable punch such that test card 110 remains stationary once it is received in punch station 170 and the punch itself aligns with the location to be punched.

Once the punch and test card are properly aligned, punch station 170 transmits punch confirmation signal 260 to punch controller 210. In turn, punch controller 210 transmits punch signal 270 to punch station 170 once punch controller 210 has received test card signal 190, punch positioning signal 240, punch ranking signal 250, punch confirmation signal 260, incubation tray signal 540 and incubation receptacle location and capacity signals 550. Signals 190, 240, 250, 260, 540 and 550 are compiled at punch controller 210 to form a single DBS tracking signal 570 which is transmitted to DBS tracking database 600 for each DBS 220.

Once punch signal 270 is received by punch station 170, the punch is activated and punches test card 110 to produce a DBS 220 which is then preferably deposited directly into an incubation receptacle on tray 560. Once the punching operation is complete, test card 110 may either be repositioned for the punching of a second or subsequent DBS 220. Alternatively, test card 110 may be discharged from test card positioner 170 into punched test card magazine 230. The punching process may repeat for the same card 110 until all of the available blood sample is punched from test card 110.

As described above, the punch mechanism contained in punch station 170 may comprise many different configurations to produce various types of DBSs 220. The punch mechanism may comprise a single die or multiple dies for punching DBSs 220 from the same test card 110. In one multiple die configuration, several DBSs 220 may be simultaneously punched or, alternatively, punched at different times. The dies may also be equipped to punch different sizes of DBSs. Also, multiple test cards 110 may be fed into multiple punch mechanisms for simultaneous punching.

In another multiple die embodiment, referred to herein as the "donut" punch mechanism, a small DBS 220 may be punched from a sample blood spot area on test card 110. A second larger DBS 220 may then be punched from the same sample blood area wherein the second DBS 220 contains an opening left by the first DBS 220 within the boundaries defined by the edges of the second DBS 220. The opening made in test card 110 by the first DBS punch may be either concentric with or eccentric to the outer edge of the second larger DBS 220. For example, a ⅛" diameter DBS 220 may be first punched from a particular blood sample area. A ¼" diameter DBS 220 may then be punched from the same area, so that the hole left by the ⅛" DBS lies within the perimeter of the ¼" DBS 220 to form a toroidal or donut shape (albeit the "hole" of the "donut" may be off center). In the case of DBSs 220 having a circular shape the shape of the opening left by the first DBS 220 would appear as a crescent shape at the perimeter of the second DBS 220. The shape and sizes of these DBSs is not critical so long as each DBS containers sufficient blood sample to conduct accurate testing of the sample.

In yet another embodiment of punch station 170, multiple separate punching mechanisms corresponding to the number of individual blood sample areas on test card 110 may be employed. Each punch is dedicated to punching one or more DBSs 220 from one of several blood sample areas on test card 110. In one embodiment, test card 110 contains three blood sample areas with one area on the first side of card 110, one area on the opposite side of card 110 and one area in the middle of card 110. Each of the three punch mechanisms employed in this embodiment are positioned in series along the machine direction which direction corresponds to the direction of travel of card 110 as it moves from reader/ comparitor 140 to punch station 170. The first punch punches a DBS 220 from the blood sample area on the first side of card 110, the second punch punches a DBS 220 from the center blood sample area and the third punch punches a DBS 220 from the second or opposite side of card. The size and shape of DBS 220 punched from each of the three punches may vary but typically the punch size and shape will be approximately ⅛" to ¼" diameter circles.

The method for selecting the appropriate area for punching DBSs may range from manual selection by an operator of a machine to semi-automatic or fully automatic means for locating the best blood sample location to punch. One such fully automated means for selecting the preferred blood sample location is optical DBS site selector 280 shown in FIG. 2. Site selector 280 may comprise any suitable vision system capable of detecting differences in the shades of colors present in the blood sample areas. Typically, dried blood samples have a reddish brown color. Generally, the darker or more intense the blood sample, the more preferable the sample is for testing purposes. Accordingly, DBS site selector 280 may identify the most favorable area of the blood sample to be punched by differentiating between the shades color present in the blood sample.

The operation of DBS site selector is as follows. Test card 110 is positioned in punch station 170. Punch station 170 detects the presence of test card 110 and transmits test card presence signal 290 to site selector 280. DBS site selector 280 optically scans the blood sample areas on test card 110 and identifies the location of the darkest shade of blood sample. Site selector 280 transmits punch positioning signal 240 (which signal 240 corresponds to the coordinates on test card 110 to be punched) to punch station controller 210 where the location to be punched is compiled and stored. Punch positioning signal 240 is transmitted from controller 210 to punch station 170 where the test card positioner positions card 110 for punching on the selected location on the card. Once the card is positioned, punch confirmation signal 260 is transmitted to controller 210. Once test card PIN signal 190, punch ranking signal 250, incubation ID signal 540 and incubation receptacle location and capacity signals 550 are received by controller 210, punch signal 270 is transmitted to punch station 170 and test card 110 is punched.

In yet another embodiment of this invention, the punch area is identified by an operator of system 100. Before test card 110 is positioned in punch station 170, the operator marks one of the designated blood sample areas to be punched on test card 110. For example, if test card 110 has three sample areas, the operator marks test card 110 with a pen or by other means to indicate which of the three sample areas will be punched. In this embodiment, no further specific selection of punched area within a single sample area is made. Test card 110 is then received in punch station 170. Punch station 170 then reads, by optical or other means, which of the three blood sample areas is to be punched. Punch station 170 then sends punch positioning signal 240 to controller 210 which stores signal 240 and transmits signal 240 to punch station 170 for punch positioning of test card 110. The punching process then proceeds from this point in the same manner as in the optical DBS site selector 280 embodiment.

In yet another embodiment of this invention, the area of test card 110 to be punched is further refined over the test card marking embodiment described above. In this embodiment, a vision system takes a real time freeze frame image of test card 110 as it travels from comparitor 140 to punch station 170. The operator views the test card image on a monitor and selects the preferred location on test card 110 to be punched. At the same time, the image is digitized and crosshairs appears on the monitor screen. The operator manipulates a monitor input device, such as a computer mouse, to move the center of the crosshairs to the location on the image which corresponds to center point of the DBS to be punched. The coordinates of this point are transmitted to controller 210 as punch positioning signal 240. Signal 240 is stored at controller 210 and then is transmitted to punch station 170 for punch positioning of test card 110. The punching process then proceeds from this point in the same manner as in the optical DBS site selector 280 embodiment.

Punching of DBSs 220 continues in a continuous automated manner regardless of the specific sample selection and punching means employed. Each DBS 220 is punched directly into an incubation receptacle 580 located on incubation tray 510. In addition to DBS and incubation tray signals 190, 250 and 540, incubation receptacle location and capacity signals 550 are exchanged between incubation tray positioner 560 and punch station controller 210. Before a DBS 220 is punched, controller 210 positions, via signal 550, an empty incubation receptacle 580 in relation to punch station 170 such that DBS 220 may be punched directly into empty receptacle 580. Positioner 560 transmits a return signal 550 to controller 210 indicating the location of receptacle 580 on tray 510 into which DBS 220 is punched. Return signal 550 also indicates to controller 210 whether incubation tray 510 has any remaining empty receptacles 580. If tray 510 does have empty receptacles 580, positioner 560 moves the next empty receptacle 580 into position for receiving the next punched DBS 220. If tray 510 does not have an empty receptacle 580 remaining, positioner 560 transports the fully populated incubation tray 510 to incubation chamber 590 where DBSs 220 are incubated for a suitable time. An empty tray 510 is then transported from bar code reader 530 to positioner 560 to receive additional DBSs 220.

Punch station controller 210 stores the incubation signals such as signal 550 which corresponds to the location of each DBS 220 on a designated incubation tray 510. Signal 550 is compiled by controller 210 along with test card PIN signal 190, punch ranking information signal 250 and incubation tray identification signal 540. These signals collectively compiled by controller 210 are transmitted to DBS tracking database 600 as DBS tracking signal 570. The information contained in DBS tracking database 600 may be accessed by central monitoring site 200 at any time to determine the precise location of any given DBS 220 from any particular test card 110. Accordingly, information may be accessed at any time from database 600 which would include test card PIN number, the number and rank of DBSs 220 punched from test card 110, the tray 510 in which each DBS 220 is located and the receptacle within tray 510 in which a particular DBS 220 is located.

Once DBSs 220 are fully incubated, trays 510 are transported from incubation chamber 590 to evaluation system 620. DBSs 220 are further tested and evaluated by system 620. The results of the evaluation conducted by system 620 for each DBS 220 are transmitted to DBS tracking database 600 as test result signal 630. The information contained in test result signal 630 is compiled in database 600 together with the other information compiled with respect to each DBS 220. Test result signal 630 may contain detailed test result information, including a final result of the testing which would indicate whether a particular blood sample contained the HIV-1 virus.

All information compiled in database 600 is collectively referred to as test result information 640. Test result information 640 is transmitted to central monitoring site 200 for reporting to the test subject who submitted test card 110.

The present invention may be embodied in other specific forms without departing from its spirit or essential attributes. Accordingly, reference should be made to the claims, rather than to the specification, for an indication of the scope of the invention.

What is claimed is:

1. An apparatus for automatically processing dried blood samples of a test subject in HIV-1 testing, wherein said blood samples are contained on a test card, said test card comprising one or more dried blood samples and a test card identification means, wherein said test card identification means identifies said test card as being associated with said blood samples, said blood samples being processed in an incubation tray receptacle of an incubation tray, said incubation tray comprising one or more incubation receptacles and a tray identification means wherein said tray identification means identifies said tray, said apparatus comprising:

a means for detecting said identification of said test card and for producing a test card identification signal corresponding to said test card identification;

a means for detecting said identification of said incubation tray and for producing a tray identification signal corresponding to said tray identification;

a means for positioning said test card for punching said dried blood samples from said test card into an incubation tray receptacle and for producing a punch confirmation signal;

a means for positioning said incubation tray for receipt of said dried blood sample, said incubation tray positioning means further comprising a means for receiving a tray repositioning signal and a means for producing a tray position signal and a dried blood sample location signal corresponding to said tray receptacle into which said dried blood sample is punched;

a means for punching said dried blood spot sample from said test card into said incubation tray receptacle upon receipt of a punch signal; and a means for controlling said punching of said dried blood spot sample, said controlling means further comprising a means for receiving said test card identification signal, a means for receiving said tray identification signal, a means for receiving said tray position signal, a means for producing said tray repositioning signal, a means for receiving said dried blood sample location signal, a means for receiving said punch confirmation signal and a means for producing said punch signal upon receipt of said punch confirmation and dried blood sample location signals.

2. The apparatus of claim 1, further comprising a means for detecting a location of said dried blood sample to be punched, said location detection means further comprising a means for producing a punch positioning signal corresponding to said location of said dried blood sample to be punched and a means for positioning said punch for punching said location, and wherein said controlling means further comprises a means for receiving said punch positioning signal.

3. The apparatus of claim 1, wherein said controller means further comprises a means for producing a dried blood sample tracking signal, said tracking signal comprising said test card identification signal, said incubation tray identification signal and said dried blood sample location signal.

4. The apparatus of claim 3, further comprising a means for storing and compiling said tracking signal in a tracking database.

5. The apparatus of claim 4, further comprising a means for incubating said dried blood samples contained in said incubation receptacles.

6. The apparatus of claim 5, further comprising a means for testing said dried blood sample in HIV-1 testing and a means for producing a test result signal corresponding to said dried blood sample.

7. The apparatus of claim 6, further comprising a means for producing a test result information signal, wherein said information signal comprises said tracking signal and said test result signal and wherein each signal corresponds to substantially the same dried blood sample.

8. The apparatus of claim 7, further comprising a means for transmitting said test result information signal to a central monitoring site for dissemination to said test subject.

9. The apparatus of claim 8, further comprising a means for comparing said test card identification with authorized test card identifications from said central monitoring site.

10. The apparatus of claim 2, further comprising a means for detecting more than one location of said dried blood sample to be punched, a means for ranking each location detected and a means for producing a punch ranking information signal.

11. The apparatus of claim 10, wherein said controlling means further comprises a means for receiving said punch ranking information signal.

12. The apparatus of claim 2, wherein said punched dried blood spot is non-circular.

13. The apparatus of claim 2, wherein said punched dried blood spot is shaped substantially as an annulus.

14. The apparatus of claim 2, wherein more than one dried blood sample may be punched from said test card.

15. An apparatus for automatically processing dried blood samples of a test subject wherein said blood samples are contained on a test card, said test card comprising one or more dried blood samples and a test card identification device wherein said identification device identifies said test card as being associated with said blood samples, said apparatus comprising:

a dried blood sample punch station, said punch station comprising a punch, a punch input device, wherein said input device receives a punch signal, and a punch signal confirmation output device, wherein said output device produces a punch confirmation signal and wherein said punch punches said blood samples from said test card upon receipt of said punch signal and wherein said dried blood samples are punched into an incubation tray receptacle of an incubation tray, said incubation tray comprising one or more incubation receptacles and a tray identification device wherein said identification device identifies said tray;

a test card identification reader, wherein said test card reader comprises a test card identification input device, wherein said input device detects said test card identification from said test card identification device, and a test card identification output device, wherein said output device produces a test card identification signal corresponding to said test card identification;

a test card transport device wherein said device transports said test card from said test card identification reader to said punch station;

an incubation tray identification reader wherein said tray reader comprises a tray identification input device, wherein said input device detects said tray identification from said tray identification device, and a tray identification output device, wherein said output device produces a tray identification signal corresponding to said tray identification;

an incubation tray positioner, wherein said positioner comprises a tray repositioning input device, wherein said input device receives a tray repositioning signal, a tray position output device wherein said output device produces a tray position signal and a dried blood sample location output device wherein said output device produces a dried blood sample location signal corresponding to said tray receptacle into which said dried blood sample is punched;

an incubation tray transport device wherein said device transports said incubation tray from said incubation tray identification reader to said incubation tray positioner; and a punch station controller, wherein said controller comprises a means for receiving said test card identification signal, a means for receiving said tray identification signal, a means for receiving said tray position signal, a means for producing said tray repositioning signal, a means fore receiving said dried blood sample location signal, a means for receiving said punch confirmation signal and a means for producing said punch signal upon receipt of said punch confirmation and dried blood sample location signals.

16. The apparatus of claim 15, further comprising a dried blood sample location selector, said selector comprising a dried blood sample location input device, wherein said input device detects a location to be punched on said test card, and a punch positioning output device, wherein said output device produces said punch positioning signal, and wherein said punch station controller further comprises a punch positioning input device wherein said input device receives said punch positioning signal.

17. A method for automatically processing dried blood samples of a test subject, wherein said blood samples are contained on a test card, said test card comprising one or more dried blood samples and a test card identification means wherein said test card identification means identifies said test card as being associated with said blood samples, said blood samples being processed in an incubation tray receptacle of an incubation tray, said incubation tray comprising one or more incubation receptacles and a tray identification means wherein said tray identification means identifies said tray, said method comprising the steps of:

reading said identification of said test card and producing a test card identification signal corresponding to said test card identification;

reading said identification of said incubation tray and producing a tray identification signal corresponding to said tray identification;

positioning said test card for punching said dried blood samples from said test card into an incubation tray receptacle and producing a punch confirmation signal;

positioning said incubation tray for receipt of said dried blood sample, receiving a tray repositioning signal, producing a tray position signal and a dried blood sample location signal corresponding to said tray receptacle into which said dried blood sample is punched;

receiving a punch signal and punching said dried blood spot sample from said test card into said incubation tray receptacle; and controlling said punching of said dried blood spot sample, said controlling step further comprising the substeps of receiving said test card identification signal receiving said tray identification signal, receiving said tray position signal, producing said tray repositioning signal, receiving said dried blood sample location signal, receiving said punch confirmation signal and producing said punch signal upon receipt of said punch confirmation and dried blood sample location signals.

18. The method of claim 17, further comprising the steps of detecting a location of said dried blood sample to be punched, producing a punch positioning signal corresponding to said location of said dried blood sample to be punched and positioning said punch for punching said location, and wherein said controlling substeps further comprise receiving said punch positioning signal.

19. The method of claim 18, further comprising the steps of producing a dried blood sample tracking signal, said tracking signal comprising said test card identification signal, said incubation tray identification signal and said dried blood sample location signal.

20. The method of claim 19, further comprising the step of storing and compiling said tracking signal in a tracking database.

21. The method of claim 20, further comprising the step of incubating said dried blood samples contained in said incubation receptacles.

22. The method of claim 18, further comprising the steps of detecting more than one location of said dried blood sample to be punched, ranking each location detected and producing a punch ranking information signal.

23. The method of claim 18, wherein said punched dried blood spot is shaped substantially as an annulus.

24. The method of claim 18, wherein more than one dried blood sample may be punched from said test card.

* * * * *